United States Patent [19]

Garrou

[11] 4,159,382
[45] Jun. 26, 1979

[54] PROCESS FOR PREPARING PICOLYLAMINE

[75] Inventor: Philip E. Garrou, Holliston, Mass.

[73] Assignee: The Dow Chemical Company, Midland, Mich.

[21] Appl. No.: 920,303

[22] Filed: Jun. 28, 1978

[51] Int. Cl.² ............................................. C07D 213/36
[52] U.S. Cl. ...................................... 546/329; 546/330
[58] Field of Search ..................................... 260/296 R

[56] References Cited

U.S. PATENT DOCUMENTS

| | | | |
|---|---|---|---|
| 2,798,077 | 7/1957 | Schlapfer et al. | 260/296 R |
| 4,080,338 | 3/1978 | Garrou et al. | 260/296 R |

*Primary Examiner*—Alan L. Rotman
*Attorney, Agent, or Firm*—L. Wayne White; J. P. Hill

[57] ABSTRACT

Picolylamines are prepared by reacting (a) cyanopyridine with (b) hydrogen in the presence of a catalytic amount of (c) a palladium on γ-alumina catalyst. The reaction is normally conducted under autogenous or superatmospheric pressure at a temperature of from 20° C. to about 75° C. in a lower alkanol (e.g., isopropanol) as the reaction medium.

8 Claims, No Drawings

PROCESS FOR PREPARING PICOLYLAMINE

BACKGROUND OF THE INVENTION

1. Field of the Invention

This is a new process for making picolylamine from cyanopyridines and hydrogen. Palladium on gamma ($\gamma$) alumina is used as the catalyst.

2. Prior Art

Volkova et al. teach that cyanopyridines are hydrogenated in the presence of palladium (or palladium on carbon) to form the corresponding picolylamines (i.e., aminomethylpyridines). See Volkova et al.: Chemical Abstracts 79:42296n; 80:120705q; 81:49570x; 83:28065n; and 83:113388q. Matsumoto et al. (*Chemical Abstracts*, 82:156097r) teach that 2,6-biscyanopyridines are hydrogenated to form the corresponding 2,6-bis(aminomethyl)pyridines as the trihydrochloride salts when the reaction is conducted over palladium on carbon using hydrochloric acid/methanol as the hydrogenation medium. These references indicate that palladium and palladium on carbon are very effective catalysts in the reaction and produce the corresponding picolylamines selectively. In USP at No. 4,080,338 a process for preparing bispicolylamine from the reaction of cyanopyridine with hydrogen in the presence of a palladium or carbon catalyst is disclosed.

SUMMARY OF THE INVENTION

We have discovered a new process for preparing picolylamines which comprises reacting by contacting under autogenous or superatmospheric pressure (a) a cyanopyridine with (b) hydrogen in the presence of a catalytic amount of (c) a palladium or $\gamma$-alumina catalyst.

DETAILED DESCRIPTION OF THE INVENTION

The instant process is represented by the following equation:

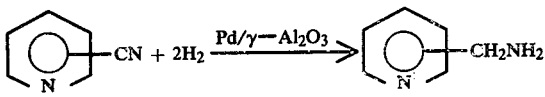

The reaction is conducted by efficiently blending the reactants and catalyst in a suitable reaction vessel (e.g., a trickle bed reactor) under autogenous or superatmospheric pressure. The reaction is exothermic and is preferably conducted in the presence of a liquid hydrogenation reaction medium. The lower alkanols of from 1 to 4 carbon atoms (e.g., methanol, ethanol, isopropanol, butanol, etc.) are normally suitable and methanol or isopropanol are preferred reaction mediums.

The reaction temperature and pressure are each independently variable and may be adjusted to convenience. Preferred rates of reaction, however, have been observed at temperatures in the range of from about 20° C. to about 100° C. (preferably from 70° C. to about 90° C.). Preferred pressures range from autogenous up to about 500 psig. Such superatmospheric pressures are normally achieved by using excess hydrogen. This excess positive pressure of hydrogen tends to maximize conversion of the cyanopyridine reactant and maximize product yield.

The reactants in this process are, of course, well-known. Any one of the three position isomers of cyanopyridine, or a mixture thereof, can be used in the instant process but 2-cyanopyridine is the most preferred reactant. Hydrogen is a gas and is normally sparged into the reaction mixture in substantial excess, as noted above.

The catalyst used herein is palladium supported on $\gamma$-alumina, normally in the form of pellets. There are many commercial sources for palladium on $\gamma$-alumina catalysts and such commercial catalysts are suitable for use herein. Alternatively, however, the catalyst can be prepared in situ by adding a soluble palladium salt along with $\gamma$-alumina to the reaction medium in which case the catalyst is generated in situ. The instant catalyst can be used repeatedly to effect high conversion of the reactants. After repeated usage, however, the catalytic activity tends to decrease and the reaction temperature and/or pressure are normally adjusted upward to off-set this decrease and maintain the high degree of conversion.

The process can be conducted batchwise or continuously. A continuous process using, for example, a trickle bed reaction is convenient and economically preferred.

EXPERIMENTAL

The following experiments further illustrate the invention.

EXAMPLE 1

A series of reactions was conducted in a trickle bed reactor vessel containing 50 g of 0.5 weight percent palladium supported on $\gamma$-alumina (as ⅛ inch tablets), supplied by Strem Chemical Company. The reaction vessel was pressurized to 350 pounds per square inch gauge (psig) and preheated to a temperature of 80° C. The liquid 2-cyanopyridine dissolved in methanol was then added dropwise onto the surface of the heated catalyst and leached through the catalyst bed for a total contact time of about 32 hours. The liquid reaction product passing from the bottom of the catalyst bed in the reactor was collected and recirculated repeatedly into and through the catalyst bed under the same conditions. At the end of 20 hours, the conversion was 100 percent of theory, based on the 2-cyanopyridine charged. The product analyzed as 74 weight percent picolylamine, 2 weight percent bispicolylamine, and 1 weight percent picolylamidine. The remaining substances were not analyzed. The same catalyst material was used in consecutive runs for Examples 1-3.

EXAMPLE 2

The same process as Example 1 was used in a consecutive run except the temperature was 75° C. and the reaction time was 4 hours. Under these conditions, the conversion was 98 percent of theory. The product analyzed comprised 80 weight percent picolylamine, 7 weight percent bispicolylamine and 3 weight percent picolylamidine.

EXAMPLE 3

The same process as Example 1 was used in a consecutive run except the temperature was 75° C., reaction time 5.5 hours and contact time 0.25 hours. The conversion was 93 percent of theory. The product analyzed comprised 73 weight percent picolylamine, 11 weight percent bispicolylamine and 4 weight percent picolylamidine.

EXAMPLE 4

The reaction was conducted in a single pass down column reactor. The catalyst (supplied by Englehard) was charged, the reactor heated to 70° C. under 500 pounds per square inch gauge of hydrogen, and the reactants added at a flow rate of 5 cc/min. of 2-cyanopyridine, 16 cc/min of isopropyl alcohol and 9 cc/min of ammonia. After 12 hours of catalyst use, the conversion was 83 percent of theory, with a product analysis of 80 weight percent of picolylamine and 12 weight percent of bispicolylamine. The remainder of the product was not identified.

What is claimed is:

1. The process for preparing picolylamine comprising reacting by contacting with thorough mixing under autogenous or superatmospheric pressure (a) a cyanopyridine with (b) hydrogen in the presence of (c) a palladium on γ-alumina catalyst.

2. The process defined by claim 1 wherein the reaction temperature is from about 20° C. to about 100° C.

3. The process defined by claim wherein said reaction is conducted in a lower alkanol of from 1 to 4 carbon atoms.

4. The process defined by claim 3 wherein said lower alkanol is methanol or isopropanol.

5. The process defined by claim 1 wherein said process is conducted under a pressure of from autogenous up to about 500 psig.

6. The process defined by claim 5 wherein said pressure is due at least in significant part to hydrogen.

7. The process defined by claim 1 wherein (a) is 2-cyanopyridine.

8. The process defined by claim 7 wherein the reaction temperature is from about 70° C. to about 90° C., the reaction pressure is from autogenous up to about 500 psig and is the result of hydrogen, and wherein the reaction is conducted in a single pass down column using methanol or isopropanol as the liquid reaction medium.

* * * * *